(12) United States Patent
Kim et al.

(10) Patent No.: US 8,785,503 B2
(45) Date of Patent: Jul. 22, 2014

(54) BIPHENYL COMPOUND OR PHARMACEUTICALLY ACCEPTABLE SALT THEREOF, METHOD FOR PREPARING NOVEL BIPHENYL COMPOUND OR PHARMACEUTICALLY ACCEPTABLE SALT THEREOF, AND PHARMACEUTICAL COMPOSITION CONTAINING SAME AS ACTIVE INGREDIENT FOR PREVENTING OR TREATING DIABETES COMPLICATIONS

(75) Inventors: Jin Sook Kim, Seoul (KR); Young Sook Kim, Daejeon (KR); Jung Hyun Kim, Seoul (KR); Eun Jin Shon, Daejeon (KR); Ki Mo Kim, Daejeon (KR); Chan-Sik Kim, Daejeon (KR); Dong Ho Jung, Daejeon (KR); Yun Mi Lee, Daejeon (KR); Kyu Hyung Jo, Daejeon (KR); Ohn Soon Kim, Daejeon (KR); Nam-Hee Yoo, Daejeon (KR)

(73) Assignee: Korea Institute of Oriental Medicine, Daejeon (KR)

( * ) Notice: Subject to any disclaimer, the term of this patent is extended or adjusted under 35 U.S.C. 154(b) by 20 days.

(21) Appl. No.: 13/816,402

(22) PCT Filed: Aug. 11, 2011

(86) PCT No.: PCT/KR2011/005913
§ 371 (c)(1),
(2), (4) Date: Apr. 18, 2013

(87) PCT Pub. No.: WO2012/021013
PCT Pub. Date: Feb. 16, 2012

(65) Prior Publication Data
US 2013/0210928 A1    Aug. 15, 2013

(30) Foreign Application Priority Data

Aug. 11, 2010  (KR) .................. 10-2010-0077117
Aug. 10, 2011  (KR) .................. 10-2011-0079856

(51) Int. Cl.
*A01N 31/14* (2006.01)
*A61K 31/075* (2006.01)

(52) U.S. Cl.
USPC .......................................... 514/721; 568/643

(58) Field of Classification Search
None
See application file for complete search history.

(56) References Cited

PUBLICATIONS

Aly, et al., "Cytotoxic Metabolites from the Fungal Endophyte Alternaria sp. and Their Subsequent Detection in Its Host Plant Polygonum senegalense," J. Nat. Prod., vol. 71, pp. 972-980, 2008.
Barros Cota, et al., "Altenusin, a biphenyl isolated from the endophytic fungus Alternaria sp., inhibits trypanothione reductase fromTrypanosoma cruzi," FEMS Microbiol. Lett vol. 285, pp. 177-182, 2008.
Kameda, et al., "An Alternative Structure for Botrallin A Metabolite of Botrytis Allii," Tetrahedron Letters No. 1, pp. 103-106, 1974.
Kuramochi, et al., "Synthesis and structure—activity relationships of dehydroaltenusin derivatives as selective DNA polymerase alpha inhibitors," Bioorganic & Medicinal Chemistry, vol. 17, pp. 7227-7238, 2009.

*Primary Examiner* — Wu-Cheng Winston Shen
*Assistant Examiner* — Jean Cornet
(74) *Attorney, Agent, or Firm* — Lucas & Mercanti, LLP

(57) ABSTRACT

The present invention provides a novel biphenyl compound or pharmaceutically acceptable salts thereof, methods for preparing the same, and pharmaceutical compositions for preventing or treating diabetic complications containing the same as an active ingredient. Novel biphenyl compounds, according to the present invention, effectively suppress generation activity of advanced glycation end products, which cause diabetic complications and are a criterion for evaluating the effectiveness of a treating agent for diabetic complications, and show an excellent therapeutic effect on retina blood vessels, increased occludin, and decreased angiogenic growth factor in actual diabetic retinopathy induced retina. Thus, novel biphenyl compounds according to the present invention can be used effectively as an active ingredient in compositions for preventing or treating diabetic complications such as diabetic retinopathy.

8 Claims, 11 Drawing Sheets

BIPHENYL COMPOUND OR PHARMACEUTICALLY ACCEPTABLE SALT THEREOF, METHOD FOR PREPARING NOVEL BIPHENYL COMPOUND OR PHARMACEUTICALLY ACCEPTABLE SALT THEREOF, AND PHARMACEUTICAL COMPOSITION CONTAINING SAME AS ACTIVE INGREDIENT FOR PREVENTING OR TREATING DIABETES COMPLICATIONS

CROSS-REFERENCES TO RELATED APPLICATION

This patent application is a 371 of PCT/KR2011/005913, filed on Aug. 11, 2011, which claims the benefit of Korean Patent Application Nos. 10-2010-0077117, filed on Aug. 11, 2010, and 10-2011-0079856, filed on Aug. 10, 2011, the contents of each of which are incorporated herein by reference.

BACKGROUND OF THE INVENTION

1. Field of the Invention

The present disclosure provides a novel biphenyl compound or pharmaceutically acceptable salts thereof, methods for preparing the same, and pharmaceutical compositions for preventing or treating diabetic complications containing the same as an active ingredient.

2. Description of the Related Art

Diabetes mellitus is one of critical adult diseases all over the world. The prevalence rate of diabetes reaches 10% in Korea, and currently, the number of diabetes patients counts more than 240,000,000 over the world and is expected to reach 380,000,000 in 2025. It was reported by Journal of American Medical Association (JAMA) in 2009 that 60% of the expected total diabetes would occur in Asia.

Particularly, the time of onset of diabetes was moved forward young adults and middle-aged people. As life-time is extended, it is very hard to avoid developing complications. In other words, after 10-20 years from the onset of diabetes, almost every body organ is damaged to cause diabetic retinopathy, diabetic cataract, diabetic nephropathy, diabetic neuropathy, diabetic heart diseases, diabetic cancers, diabetic osteoporosis, etc.

Chronic diabetic nephropathy becomes the most critical reason of hemodialysis treatment and end stage renal disease. Diabetic cataract and diabetic retinopathy cause sight loss and even lead to death. In USA, the major reason of sight loss in the age group of 25-74 is diabetes and 60% of diabetics lose their eye sight 15-20 years after the onset (Klein R., 1996, *Annu. Rev. Public. Health.* 66:366-78). In addition, diabetic retinopathy becomes the leading cause of blindness in adults, and the prevalence rate is rising (Sharkey T. P., 1971, *J. Am. Diet. Ass.* 58:528).

Therefore, only if the occurrence of complications is postponed 5-10 years, the quality of lives of diabetics and their families will be totally different, affecting significantly the national budget itself.

Representative factors that cause diabetic complications are as follows.

It was known that in a long-term hyperglycemic environment, advanced glycation endproducts (AGE) formed by nonenzymatic glycation of protein bind to proteins or lipids abnormally and irreversibly and activate receptors for advanced glycation endproducts (RAGE) abnormally, leading to develop diabetic complications.

Nonenzymatic glycation of protein indicates a condensation reaction of reducing sugars and amino acid groups such as lysine residue of protein, which is the Maillard reaction, without being mediated by an enzyme. As a result of this reaction, advanced glycation endproducts (AGE) are generated.

That is, nonenzymatic glycation of protein can be divided into two steps: (1) wherein amino acid groups such as lysine residue of protein react with aldehydes or ketones of reducing sugars without enzyme activity, which is a nucleophilic addition reaction, to produce the early stage product Schiff bases, and then ketoamine adducts residing close to the Schiff base react with each other by condensation to produce reversible Amadori type early glycation products; and (2) wherein when hyperglycemia status continues, the reversible Amadori type early glycation products are not degraded and rearranged to produce irreversible AGE, and the generated irreversible AGE are conjugated or cross-linked with proteins or lipids, leading to the generation of irreversible glycoprotein or glycolipids.

Unlike the reversible Amadori type early glycation products, AGE are irreversible reaction products and once generated, they are not degraded even when the blood glucose level is recovered to normal, and are accumulated in tissues as long as proteins or lipids to which AGE are conjugated survive, resulting in abnormal changes in structure and functions of tissues to cause complications all over tissues (Vinson, J. A. et al., 1996, *J. Nutritional Biochemistry* 7: 559-663; Smith, P. R. et al., 1992, *Eur. J. Biochem.*, 210: 729-739).

For example, glycated albumin, one of AGE generated by the reaction between glucoses and many kinds of proteins, plays a critical role in causing chronic diabetic nephropathy. Glycated albumin can be introduced into glomerular cells more easily than normal albumin and high concentration of glucose stimulates mesangium cells to increase extracellular matrix synthesis. Due to excessively introduced glycated albumin and increased extracellular matrix, glomerular fibrosis is induced. By such a mechanism, glomerulus is continuously damaged, and at last, there is no choice but to use extreme therapeutic methods such as hemodialysis or organ transplantation.

In addition, it has been reported that due to chronic diabetes, collagens are conjugated with AGE in arterial wall and basement membrane proteins are conjugated with AGE in glomerulus, which are accumulated in tissues (Brownlee, M., et al., 1986, *Sciences*, 232, 1629-1632).

Such nonenzymatic glycation of protein induces glycosylation of basement membrane, proteins such as plasma albumin, lens protein, fibrin, collagen, etc. and AGE generated thereby causes abnormal changes in the structure and functions of tissues, leading to chronic diabetic complications such as diabetic retinopathy, diabetic cataract, diabetic nephropathy, diabetic neuropathy, etc.

Like this, the mechanisms of nonenzymatic glycation are all connected to cause diabetic complications. Thus, it was revealed that it is very important to inhibit AGE formation in order to postpone, prevent or treat diabetic complications (Brownlee, M., et al., 1988, *N. Engl. Med.*, 318, 1315-1321).

Currently, a protein glycosylation inhibitor and a synthetic medicine, aminoguanidine is a nucleophilic hydrazine and binds to Amadori products to prevent cross-linking with proteins, resulting in the inhibition of AGE formation, by which it can postpone or prevent the progress of diabetic complications (Brownlee, M., et al., 1986, *Science*, 232, 1629-1632; Edelstein, D. et al., 1992, *Diabetes*, 41, 26-29). Aminoguanidine is the most promising synthetic medicine for the prevention and treatment of diabetic complications, and the third phase clinical test has been completed. However, the clinical test of aminoguanidine has been stopped because of its toxicity observed during the long term administration. Accordingly, there is a need to develop a safer and more effective natural medicine.

For diabetic retinopathy, chronic retinal hypoxia, retinal ischemia, and an increased vascular permeability induce vitreous hemorrhage and eventually macular edema or angiogenesis, resulting in progress into proliferative diabetic retinopathy (Aiello L. P., *Diabetes Care.* 21:143-156). In this process, various causes are involved, and particularly, angiogenic growth factors which are known to be angiogenic factors and vascular permeability factors are seemed to play the most critical role. Angiogenic growth factors are expressed by early changes in diabetic retinopathy, and tight junction proteins such as occludin decrease, and eventually, the breakdown of blood-retinal barrier which is a physical barrier of retina increases blood permeability and aggravates retinopathy (Wang. W., 2001, *Am. J. Physiol. Heart. Circ. Physiol.* 280; H434-40).

There is still no drug of which effectiveness in preventing diabetic retinopathy or inhibiting the progression is proved. However, there is an attention being paid to development of an inhibiting agent against various growth factors, which are involved in angiogenesis, among many mechanisms for generating retinopathy.

Examples of current therapy for diabetic retinopathy include laser therapy and vitrectomy, etc. Most therapies are surgical and drug treatment is still being developed. The current drug treatment, intravitreal injection is often being carried out as a primary or additional treatment. Intravitreal injection causes direct and relatively rapid effects. The representative drug is angiogenesis inhibitors, and researches and therapeutic development on angiogenesis inhibitors are being actively conducted. Steroids inhibit the formation of vascular growth factors such as angiogenic growth factors which increase blood permeability, block the arachidonic acid pathway, and inhibit the formation of prostaglandins, and thus, are very effective for macular edema via anti-inflammatory function and blood-retinal barrier stabilization (Sutter F. K., 2004, *Ophthalmology,* 111: 2044-9). Recently, there have been reports that intravitreal injection of the anti-angiogenic growth factor (anti-VEGF) reduces macular edema caused by central retinal vein occlusion, and reduces blood permeability and fibrovascular proliferation in proliferative diabetic retinopathy (Avery R. L., 2006, *Ophthalmology,* 113:363-72; Spaide R. F., 2006, *Retina,* 26:275-8; Iturralde D., 2006, *Retina,* 26:279-84). However, Avastin is approved by the FDA as an anticancer agent, not for ocular uses. Like steroids, the effect would last only several months, and in some cases, the drug may cause cataract or glaucoma and require additional therapies. Accordingly, many researches have been proceeded to develop anti-angiogenic growth factors from foods or natural products which have no side effects.

Thus, the present inventors have performed researches to develop new therapeutic agents for diabetic complications derived from natural products, isolated a novel biphenyl compound from a medical herb *Osteomeles schwerinae* Schneid and identified that these compounds can be effectively used for the prevention or treatment of diabetic complications since these have inhibited AGE formation both in vitro and animal experiments (in vivo) and prevented significantly abnormal change in the tight junction protein occludin and VEGF, the early symptoms of diabetic retinopathy, thereby leading to completion of the present invention.

SUMMARY OF THE INVENTION

One object of the present invention is to provide a novel biphenyl compound.

Another object of the present invention is to a method for preparing the novel biphenyl compound.

Still another object of the present invention is to provide a pharmaceutical composition for preventing or treating diabetic complications, containing the novel biphenyl compound or pharmaceutically acceptable salts thereof as an active ingredient.

Even another object of the present invention is to provide a pharmaceutical composition for preventing or treating a diabetic cancer, containing the novel biphenyl compound as an active ingredient.

Yet another object of the present invention is to provide a health food composition for preventing or ameliorating diabetic complications, containing the novel biphenyl compound as an active ingredient.

Further another object of the present invention is to provide a health food composition for preventing or ameliorating diabetic cancers, containing the novel biphenyl compound as an active ingredient.

In order to achieve the objects, the present invention provides a novel biphenyl compound represented by the following Chemical Formula 1:

[Chemical Formula 1]

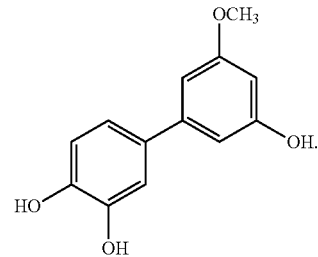

The present invention also provides a method of preparing a novel biphenyl compound, the method comprising the steps of:

(1) extracting *Osteomeles schwerinae* Schneid with water, an alcohol, or a mixture thereof to obtain *Osteomeles schwerinae* Schneid extract;

(2) suspending the *Osteomeles schwerinae* Schneid extract obtained from step (1) in water and then obtaining n-hexane, ethyl acetate, and n-butanol fractions of *Osteomeles schwerinae* Schneid by stepwise using n-hexane, ethyl acetate and n-butanol as an extraction solvent;

(3) carrying out a silica gel column chromatography on the ethyl acetate fraction of *Osteomeles schwerinae* Schneid obtained from step (2) to separate and purify an active fraction; and (4) carrying out Sephadex LH-20 column chromatography on the active fraction obtained from step (3) to separate and purify the compound represented by Chemical Formula 1.

Furthermore, the present invention provides a pharmaceutical composition for preventing or treating diabetic complications, the composition containing the novel biphenyl compound or pharmaceutically acceptable salts thereof as an active ingredient.

The present invention also provides a pharmaceutical composition for preventing or treating cancers containing the novel biphenyl compound as an active ingredient.

Furthermore, the present invention provides a health food composition for preventing or ameliorating diabetic complications containing the novel biphenyl compound as an active ingredient.

The present invention also provides a health food composition for preventing or ameliorating cancers containing the novel biphenyl compound as an active ingredient.

Novel biphenyl compounds of the present invention have excellent activity to inhibit formation of advanced glycation end products, which are a criterion for evaluating the effectiveness of a treating agent for diabetic complications, and show an excellent therapeutic effect on retina blood vessels, increased occludin, and decreased angiogenic growth factor in actual diabetic retinopathy induced retina. Thus, novel biphenyl compounds according to the present invention can be used effectively as an active ingredient in compositions for preventing or treating diabetic complications such as diabetic retinopathy.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
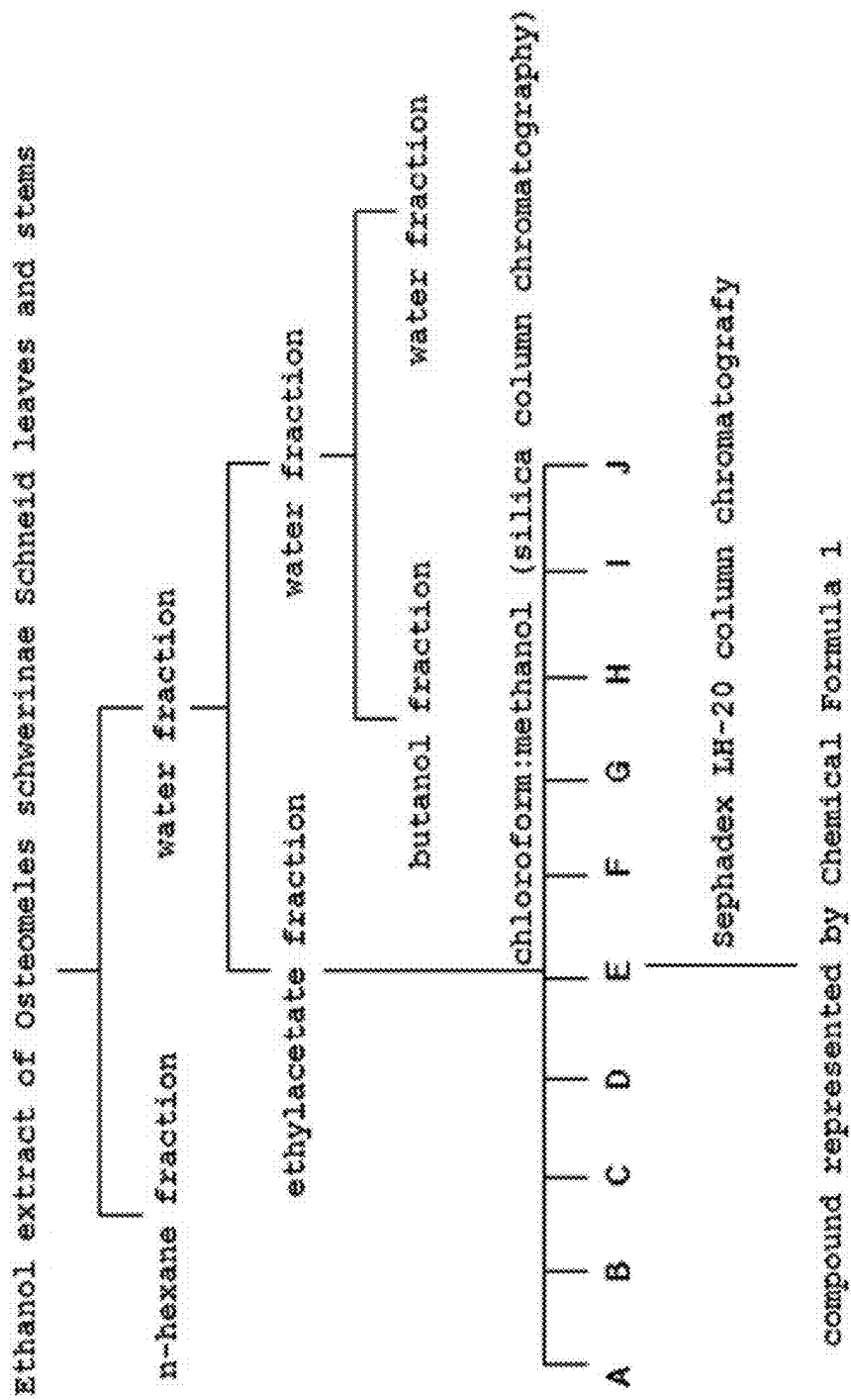
FIG. 1 is a diagram illustrating fractionation according to one example of the present invention.
Figure 2:
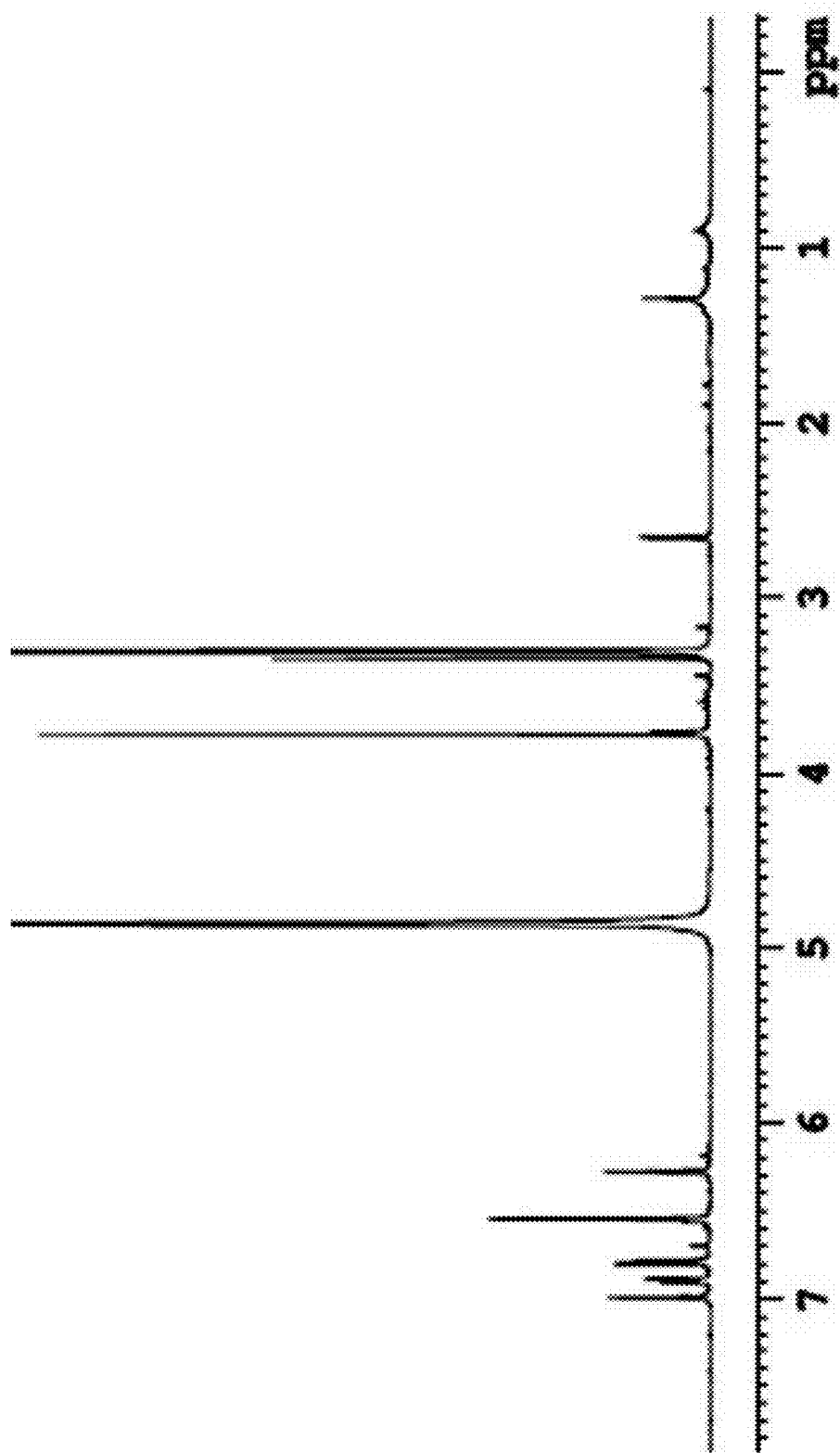
FIG. 2 is the $^1$H-NMR spectrum for the compound of Chemical Formula 1 according to one example of the present invention.
Figure 3:
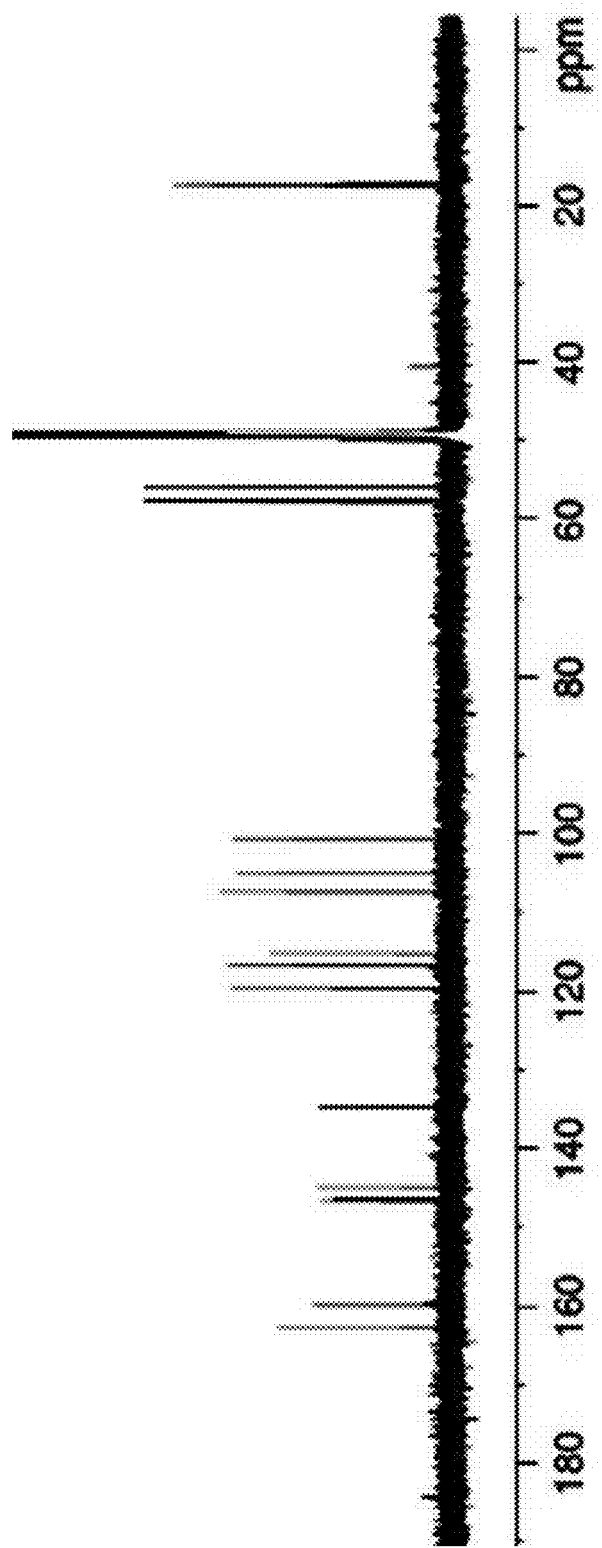
FIG. 3 is the $^{13}$C-NMR spectrum for the compound of Chemical Formula 1 according to one example of the present invention.
Figure 4:
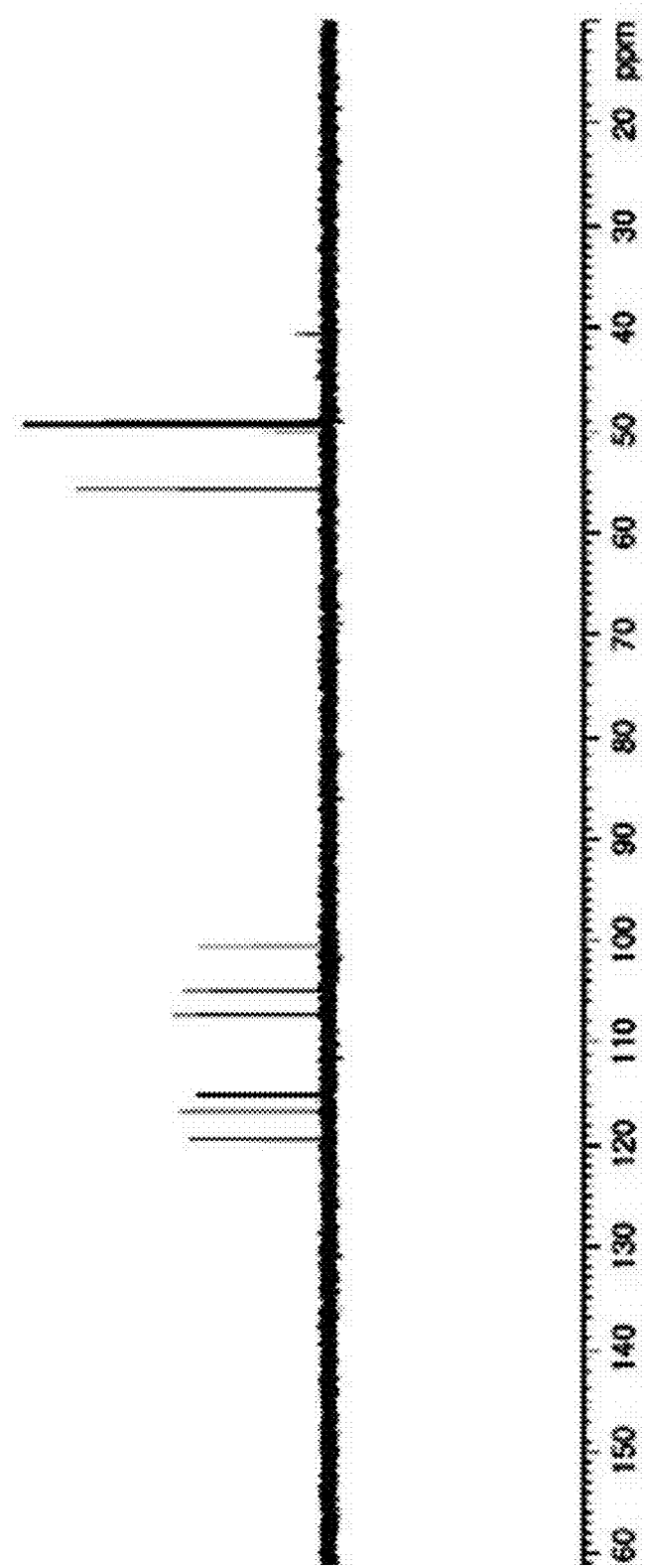
FIG. 4 is the DEPT 135 spectrum for the compound of Chemical Formula 1 according to one example of the present invention.
Figure 5:
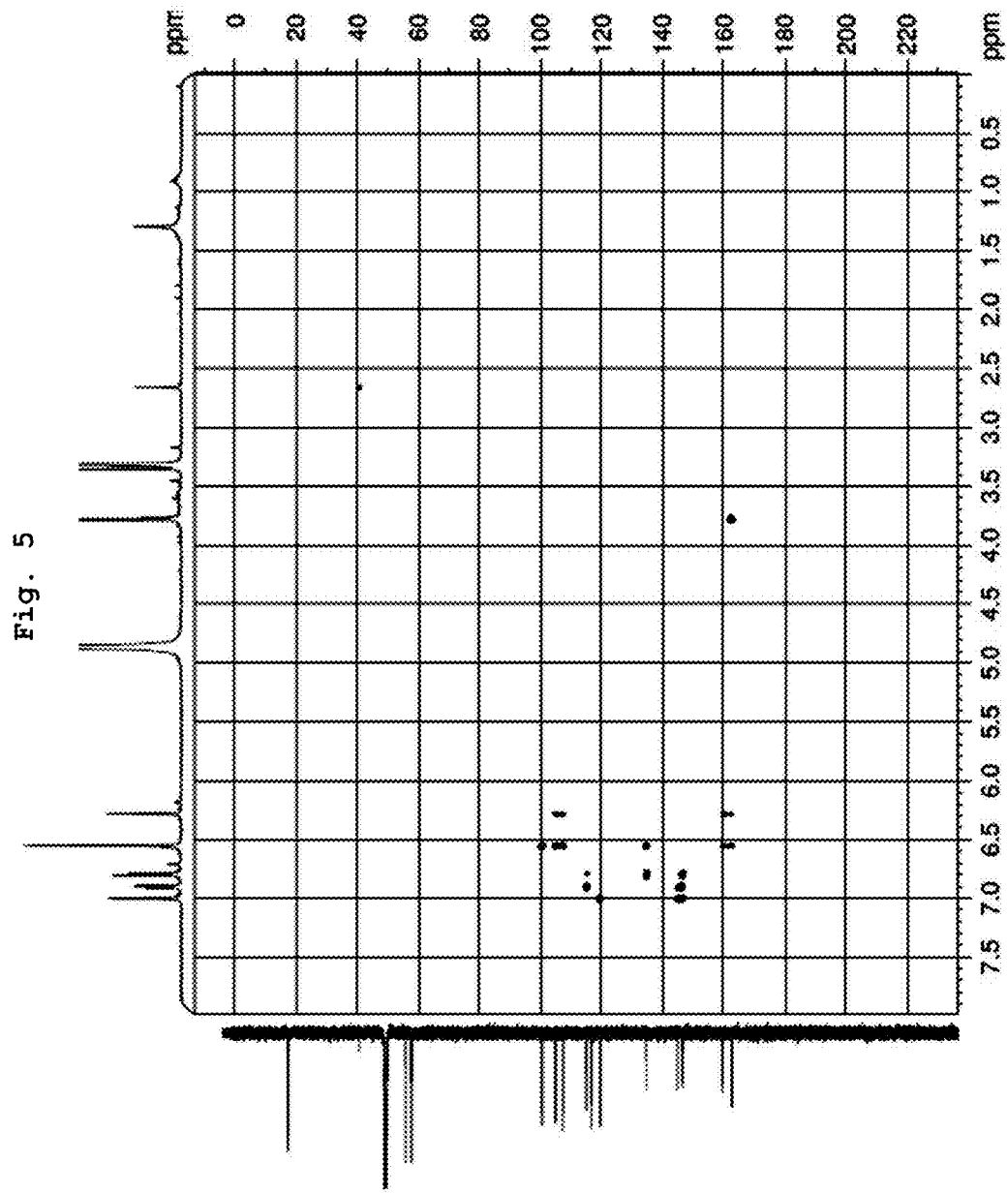
FIG. 5 is the $^{13}$C-$^1$H NMR HMBC spectrum for the compound of Chemical Formula 1 according to one example of the present invention.

Hereinafter, the present invention will be described in detail.

The present invention provides a compound represented by the following Chemical Formula 1 or pharmaceutically acceptable salts thereof.

[Chemical Formula 1]

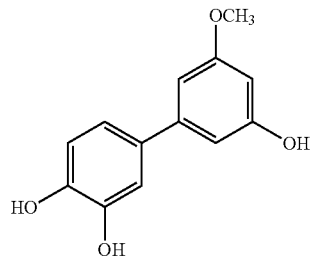

The present invention includes not only the novel biphenyl compound represented by Chemical Formula 1, but also pharmaceutically acceptable salts thereof, and all the possible solvates, hydrates, racemates, or stereoisomers, which may be prepared from the compound of Chemical Formula 1 or pharmaceutically acceptable salts thereof.

The novel biphenyl compound of the present invention, represented by the Chemical Formula 1, may be used in the form of pharmaceutically acceptable salts. Useful salts are acid addition salts, which are formed by pharmaceutically acceptable free acids. The acid addition salts are obtained from inorganic acid, such as hydrochloric acid, nitric acid, phosphoric acid, sulfuric acid, hydrobromic acid, hydroiodic acid, nitrous acid or phosphorous acid, and nontoxic organic acids, such as aliphatic mono- and dicarboxylates, phenyl-substituted alkanoates, hydroxyalkanoates, alkanedioates, aromatic acids, aliphatic and aromatic sulphonic acids. Such pharmaceutically nontoxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylenesulfonate, phenyl acetate, phenylpropionate, phenylbutyrate, citrate, lactate, hydroxybutyrate, glycolate, malate, tartrate, methane sulfonate, propane sulfonate, naphthalene-1-sulfonate, naphthalene-2-sulfonate or mandelate.

Acid addition salts according to the present invention may be prepared using a conventional method. For example, they may be prepared by dissolving the compound of Chemical Formula 1 in an excess acid aqueous solution and precipitating its salt with the use of a water-miscible organic solvent, such as methanol, ethanol, acetone, or acetonitrile.

These acid addition salts may be prepared by heating the same amounts of novel biphenyl compound of Chemical Formula 1 and an acid aqueous solution or alcohol, and then evaporating this mixture to dry or by suctioning and filtering the precipitates.

Also, pharmaceutically acceptable metallic salts may be prepared by using a base. Alkali metal or alkali earth metal salts are obtained, for example, by dissolving the compound in an excessive alkali metal hydroxide or alkali earth metal hydroxide solution, filtering non-soluble compound salts, and evaporating to dry residual solvent. For the metallic salt, preparing sodium salt, potassium salt or calcium salt are suitable for medicine manufacture.

The present invention also provides a method for preparing the novel biphenyl compound.

The novel biphenyl compound according to the present invention may be prepared by a method comprising the steps of:

(1) extracting *Osteomeles schwerinae* Schneid with water, an alcohol, or a mixture thereof to obtain *Osteomeles schwerinae* Schneid extract;

(2) suspending the *Osteomeles schwerinae* Schneid extract obtained from step (1) in water and then obtaining n-hexane, ethyl acetate, and n-butanol fractions of *Osteomeles schwerinae* Schneid by stepwise using n-hexane, ethyl acetate and n-butanol as an extraction solvent;

(3) carrying out a silica gel column chromatography on the ethyl acetate fraction of *Osteomeles schwerinae* Schneid obtained from step (2) to separate an active fraction; and (4) carrying out Sephadex LH-20 column chromatography on the active fraction obtained from step (3) to obtain the compound of Chemical Formula 1.

Hereinafter, the preparation method of the present invention will be described step-by-step (see FIG. 1).

Step (1) according to the present invention is obtaining the *Osteomeles schwerinae* Schneid extract, which may be prepared specifically by carrying out the following steps:

(a) adding an extraction solvent to *Osteomeles schwerinae* Schneid and extracting *Osteomeles schwerinae* Schneid with the extraction solvent;

(b) cooling and filtering the extract of step (a); and (c) concentrating under reduced pressure and drying the filtered extract of step (b).

In the step (1), the extraction solvent of step (a) may be water, an alcohol, or a mixture thereof. For the alcohol, a lower alcohol of $C_1$ to $C_4$ is preferable, and ethanol or methanol is more preferable, and ethanol is most preferable, however, the present invention is not limited thereto. The extraction method may be conventional methods in the art, such as filtration, hot water extraction, immersion extraction, refluxing/cooling extraction, ultrasonic extraction, etc. Extraction may be repeated three times, however, the present invention is not limited thereto. The extraction solvent may be added in an amount of 1 to 10 times, preferably 1 to 5 times, of the weight of dried *Osteomeles schwerinae* Schneid stems. Extraction temperature may be, but is not limited to, 20 to 30° C. Extraction time may be, but is not limited to, 24 to 48 hours.

In the step (2), concentration under reduced pressure may use vacuum concentrators or vacuum rotary evaporators, but the present invention is not limited thereto. In addition, drying may be reduced pressure drying, vacuum drying, boil drying, spray drying or freeze drying, but the present invention is not limited thereto.

Step (2) according to the present invention is obtaining n-hexane, ethyl acetate, and n-butanol fractions of *Osteomeles schwerinae* Schneid by stepwise fractionating the *Osteomeles schwerinae* Schneid extract obtained from step (1) with n-hexane, ethyl acetate and n-butanol.

In one Example according to the present invention, a n-hexane fraction may be obtained by adding water and n-hexane to an alcohol extract such as a methanol or ethanol extract of *Osteomeles schwerinae* Schneid prepared from step (1), fractionating a water layer and an organic layer by using a separatory funnel, concentrating the organic layer fraction under reduced pressure by using a vacuum evaporator.

Then an ethyl acetate fraction may be obtained by adding ethyl acetate to the water layer, fractionating a water layer and an organic layer by using a separatory funnel, concentrating the obtained organic layer fraction under reduced pressure by using a vacuum evaporator; and a n-butanol fraction may be obtained by adding n-butanol to the water layer, fractionating a water layer and an organic layer by using a separatory funnel, concentrating the obtained organic layer fraction under reduced pressure by using a vacuum evaporator.

Step (3) according to the present invention is separating an active fraction by carrying out a silica gel column chromatography on the ethyl acetate fraction of *Osteomeles schwerinae* Schneid obtained from step (2).

In one Example according to the present invention, ten fractions (A-J) were separated by carrying out a silica gel column chromatography using a mixed solvent of chloroform and methanol (40:1-0:1) as an elution solvent on the ethyl acetate fraction among fractions obtained from step (2) and among ten fractions, the fraction E (chloroform:methanol=10:1, v/v) was used as an active fraction for the next step.

Step (4) according to the present invention is carrying out Sephadex LH-20 column chromatography on the active fraction obtained from step (3) to obtain the compound of Chemical Formula 1.

In one Example according to the present invention, the compound represented by Chemical Formula 1 of the present invention may be obtained by loading the active fraction obtained from step (3) into a column packed with Sephadex LH-20, carrying out a column chromatography using a mixed solvent of methanol and distilled water (1:1-1:0, v/v) as an elution solvent, and separating.

In addition, the present invention provides a pharmaceutical composition for preventing or treating diabetic complications containing the biphenyl compound or pharmaceutically acceptable salts thereof as an active ingredient.

The inhibitory effect of the compound of Chemical Formula 1 according to the present invention on formation of AGE, which are an indicator of diabetic complications and indicator of treatment efficiency assessment, was determined and the result indicated that the experimental group treated with the compound of Chemical Formula 1 of the present invention showed very effective inhibitory effect on AGE formation compared to the known aminoguanidine (see Experimental Example 1 and Table 2).

In addition, an animal experiment (in vivo) was carried out to determine the therapeutic effect of the compound of Chemical Formula 1 on retina in which diabetic retinopathy, one example of diabetic complications, was induced. As a result, the blood-retinal barrier was broken down in the diabetic retinopathy-induced group, while the group treated with the compound of Chemical Formula 1 showed the dose-dependent amelioration of symptoms. Changes in occludin, the protein which constitutes the tight junction for protecting eyes, were determined. As a result, the diabetic retinopathy-induced group showed a dose-dependent decrease in occludin while the experimental group treated with compound of Chemical Formula 1 showed a dose-dependent increase in occludin (see Experimental Example 2 and FIGS. 6-8).

Furthermore, changes in retinal blood vessels were observed. As a result, the avascular area was small and the increase in length by vascular tortuosity was reduced in the experimental group treated with the compound of Chemical Formula 1 of the present invention. Changes in an angiogenic growth factor were determined and the result indicated that the diabetic retinopathy-induced group showed a dose-dependent increase in the angiogenic factor while the experimental group treated with the compound of Chemical Formula 1 showed a dose-dependent decrease in the angiogenic factor (see Experimental Example 3 and FIGS. 9-11).

Accordingly, since the novel biphenyl compound (the compound of Chemical Formula 1) of the present invention has excellent activity to inhibit formation of advanced glycation end products, which are a criterion for evaluating the effectiveness of a treating agent for diabetic complications, and shows an excellent therapeutic effect on retina blood vessels, increased occludin, and decreased angiogenic growth factor in actual diabetic retinopathy induced retina, it can be used effectively as an active ingredient in the composition for preventing or treating diabetic complications such as diabetic retinopathy.

In the present invention, examples of diabetic complications include diabetic retinopathy, diabetic cataract, diabetic nephropathy, diabetic neuropathy, diabetic heart diseases, diabetic osteoporosis, or diabetic atherosclerosis, etc.

Diabetic complications are symptoms that can occur as a result of having diabetes over a long time. However, standards of onset or determination of diabetic complications are different from those of diabetes and therapeutic agents for diabetic complications may be used separately from therapeutic agents for diabetes.

Furthermore, the present invention provides a pharmaceutical composition for preventing or treating diabetic cancers containing the biphenyl compound or pharmaceutically acceptable salts thereof as an active ingredient.

It has already been reported that AGE cause cancers (Tokuda H. et al., 2005, *Book of Abstract of* 53rd *GA Congress joint with SIF*, P076), and since the biphenyl compound or pharmaceutically acceptable salts thereof of the present invention inhibit AGE formation effectively, they can be used effectively in pharmaceutical compositions for preventing or treating diabetic cancers (see Experimental Example 1 and Table 2).

The composition containing the novel biphenyl compound of the present invention may comprise 0.1 to 50% by weight of the compound with respect to total weight of the composition; however, the present invention is not limited to such.

The composition of the present invention may further comprise suitable carriers, excipients, and diluents that are conventionally used for the preparation of pharmaceutical preparations.

The composition according to the present invention may be used as oral formulations such as powders, granules, tablets, capsules, suspensions, emulsions, syrup, aerosols, etc., external formulations, suppositories, and sterile injections by respective conventional methods. Examples of carriers, excipients, and diluents that may be comprised in the composition of the present invention include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate, and mineral oil.

Formulations may prepared by using diluents or excipients such as fillers, extenders, binders, humectants, disintegrators, surfactants, etc. that are generally used. Solid formulations for oral administration include tablets, pills, powders, granules, capsules, etc. and these solid formulations are prepared by mixing at least one or more excipients, for example, starch, calcium carbonate, sucrose or lactose, gelatin, etc. with the composition of the present invention. Also, lubricants such as magnesium stearate, talc, etc. are used in addition to simple excipients. Liquid formulations for oral administration include suspensions, liquid for internal use, emulsions, syrups, etc., and various excipients such as humectants, sweeteners, aromatics, preservatives, etc. in addition to generally-used simple diluents such as water and liquid paraffin may be included. Formulations for parenteral administration include sterile aqueous solutions, non-aqueous solvents, suspensions, emulsions, freeze-dried formulations, and suppositories. Propylene glycol, polyethylene glycol, vegetable oil such as olive oil, and injectable ester such as ethylolate, etc. may be used for non-aqueous solvents and suspensions. Witepsol, macrogol, tween 61, cacao butter, laurin butter, glycerogelatin, etc. may be used for a suppository base.

The composition of the present invention may be administered orally or parenterally and any methods may be used for administration as long as they are parenteral.

The preferred administration dose of the composition of the present invention depends on condition and body weight of a patient, severity of disease, drug form, administration route, and administration period, and may be selected appropriately by those skilled in the art.

The composition of the present invention may be used alone or in combination with surgery, radiation therapy, hormonal therapy, chemical therapy, and methods using biological regulators.

The present invention also provides a health food composition for preventing or ameliorating diabetic complications containing the biphenyl compound or pharmaceutically acceptable salts thereof as an active ingredient.

Since the novel biphenyl compound represented by Chemical Formula 1 of the present invention has excellent activity to inhibit formation of advanced glycation end products, which are a criterion for evaluating the effectiveness of a treating agent for diabetic complications (see Experimental Example 1 and Table 2), and shows an excellent therapeutic effect on retina blood vessels, increased occludin, and decreased angiogenic growth factor in actual diabetic retinopathy induced retina (see Experimental Examples 2 and 3 and FIGS. 6-11), it can be used effectively as an active ingredient in the composition for preventing or ameliorating diabetic complications such as diabetic retinopathy.

In the present invention, examples of diabetic complications include diabetic retinopathy, diabetic cataract, diabetic nephropathy, diabetic neuropathy, diabetic heart diseases, diabetic osteoporosis, or diabetic atherosclerosis, etc.

Diabetic complications are symptoms that can occur as a result of having diabetes over a long time. However, standards of onset or determination of diabetic complications are different from those of diabetes.

Further, the present invention provides a pharmaceutical composition for preventing or treating diabetic cancers containing the biphenyl compound or pharmaceutically acceptable salts thereof as an active ingredient.

It has already been reported that AGE cause cancers (Tokuda H. et al., 2005, *Book of Abstract of* 53rd *GA Congress joint with SIF*, P076), and since the biphenyl compound or pharmaceutically acceptable salts thereof of the present invention inhibit AGE formation effectively, they can be used effectively in health food compositions for preventing or ameliorating diabetic cancers (see Experimental Example 1 and Table 2).

The novel biphenyl compound may be added to health supplement foods such as foods, beverages, etc. with the purpose of preventing or ameliorating diabetic complications or cancers.

There are no specific limitations on the kinds of the foods. Examples of foods to which the compound may be added include drinks, meats, sausages, breads, biscuits, rice cakes, chocolates, candies, snacks, confectioneries, pizzas, instant noodles, other noodles, gums, dairy products including ice creams, various soups, beverages, alcoholic drinks and vitamin complexes, milk and other products, etc. and all foods which are health functional in a common sense.

The novel biphenyl compound of the present invention may be added to foods alone or in combination with other foods or food ingredients, and suitably used according to a conventional method. The amount of addition of the active ingredient can be suitably determined depending on the use purpose (prevention or amelioration). Generally, in the preparation of health foods, the compound may be added in an amount of 0.1 to 90 parts by weight of total food weight. However, for the purpose of health and hygiene or in the case of long-term intake for health control, the amount may be lower than the above-described range. Since there is no problem in view of safety, the active ingredient may also be used in a higher amount than the above-described range.

The health functional beverage composition of the present invention has no particular limitation to other ingredients except that it comprises the indicated ratio of the compound as an essential ingredient, and like conventional beverages, it may comprise additional ingredients such as various flavoring agents or natural carbohydrates. Examples of the above described natural carbohydrates include monosaccharides such as glucose and fructose, disaccharides such as maltose and sucrose, polysaccharides, for example, general sugars such as dextrin and cyclodextrin, and sugar alcohols such as xylitol, sorbitol, erythritol, etc. In addition to the above-described flavoring agents, natural flavoring agents such as thaumatin and *stevia* extracts, e.g., rebaudioside A, glycyrrhizin, etc., and synthetic flavoring agents such as saccharin and aspartame may be used favorably for the flavoring agents. The ratio of the natural carbohydrate is generally about 1 to 20 g per 100 g of the composition of the present invention, preferably about 5 to 12 g.

In addition to that, the composition containing the biphenyl compound of the present invention may contain various nutritional supplements, vitamins, minerals (electrolytes), synthetic and natural flavors, colorants and fillers (cheese, chocolates, etc.), pectic acid and its salt, alginic acid and its salt, organic acids, protective colloidal thickeners, pH regulating agents, stabilizers, preservatives, glycerin, alcohols, carbonizing agents used in carbonated drinks, etc. Moreover, the composition containing the biphenyl compound of the present invention may contain fruit flesh for the preparation of natural fruit juices, fruit juice beverages, and vegetable beverages.

These ingredients may be used alone or in combination. Although not critical, these additives are generally used in an amount from about 0.01 to about 20 parts by weight, based on 100 parts by weight of the novel biphenyl compound isolated from *Osteomeles schwerinae* Schneid of the present invention.

The present invention also provides a method for preventing or treating diabetic complications, the method comprising administering the novel biphenyl compound or pharmaceutically acceptable salts thereof to a patient in need thereof.

Furthermore, the present invention provides the novel biphenyl compound or pharmaceutically acceptable salts, which are used for preventing or treating diabetic complications.

Hereinafter, the present invention will be described in more detail with reference to the following examples.

However, the following examples are provided for illustrative purposes only, and the scope of the present invention should not be limited thereto in any manner.

Example 1

Biphenyl Compound Preparation

Step 1: Preparation of *Osteomeles schwerinae* Schneid Extract 4.0 kg of the dried in the shade *Osteomeles schwerinae* Schneid leaves and stems was prepared by cutting finely. 12 L of ethanol was added to the prepared *Osteomeles schwerinae* Schneid leaves and stems and extraction was carried out at room temperature for 24 hours and the extract was filtered. The extraction and filtration process was repeated three times. The obtained extract was concentrated by using a vacuum evaporator and 104 kg of the ethanol extract of *Osteomeles schwerinae* Schneid was obtained.

Step 2: Preparation of *Osteomeles schwerinae* Schneid Fraction 500 mL of water and 500 mL of n-hexane were added to the *Osteomeles schwerinae* Schneid ethanol extract prepared in step 1, and a water layer and an organic layer were fractionated by using a separatory funnel, and the organic layer fraction was concentrated under reduced pressure by using a vacuum evaporator to obtain 6.30 g of a n-hexane fraction.

500 mL of ethyl acetate was added to the water layer, and a water layer and an organic layer were fractionated by using a separatory funnel, and the obtained organic layer fraction was concentrated under reduced pressure by using a vacuum evaporator to obtain 27.0 g of an ethyl acetate fraction. 500 mL of n-butanol was added again to the water layer, and a water layer and an organic layer were fractionated by using a separatory funnel, and the obtained organic layer fraction was concentrated under reduced pressure by using a vacuum evaporator to obtain 10.08 g of a n-butanol fraction.

The experiment for analyzing an inhibitory effect on AGE formation showed that the ethyl acetate fraction exhibited 16.61 µg/mL of $IC_{50}$ and had the most excellent inhibitory effect on AGE formation among those fractions.

Step 3: Preparation of Active Fraction

Among fractions obtained from step 2, 27.0 g of the ethyl acetate fraction, which has the most excellent inhibitory effect on AGE formation, was loaded into a column (7×57 cm, diameter) packed with 70-230 mesh silica gel and a silica gel chromatography was carried out using a mixed solvent of chloroform and methanol (a concentration gradient of 40:1-0:1, v/v) as an elution solvent and ten fractions were obtained (A-J). Among them, the fraction E was selected for an active fraction for the next step.

Step 4: Biphenyl Compound Isolation 700 mg of the active fraction E obtained from step 3 was loaded into a column packed with Sephadex LH-20 gel and a column chromatography was carried out using a mixed solvent of methanol and distilled water (1:1-1:0, v/v) as an elution solvent. As a result of isolation, the novel biphenyl compound was isolated.

Novel Biphenyl Compound Identification

For analyzing the structure of the compound obtained from step 4, NMR analysis and mass spectrometry were carried out. Molecular weight and molecular formula were determined by HRESIMS measurement using a Shimadzu LCMS-IF-TOF mass spectrometer. The structure was identified as the following Chemical Formula 1 through analyses of $^1$H-NMR and $^{13}$C-NMR spectra using Varian 400 NMR and DEPT spectrum. Analyses results are shown in FIGS. 2-5 and Table 1.

TABLE 1

| Structure | Spectroscopic analysis | Data |
|---|---|---|
| [Chemical Formula 1]<br><br>structure with OCH₃, OH, HO, OH groups on biphenyl | HRESIMS<br>$^1$H NMR<br><br><br><br><br><br><br>$^{13}$C NMR | 231.0663 [M − H]$^-$<br>$^1$H-NMR (300 MHz, CD$_3$OD) δ 7.00 (1H, d, J = 2.0 Hz, H-2), 6.90 (1H, dd, J = 8.0, 2.0 Hz, H-6), 6.79 (1H, d, J = 8.5 Hz, H-5), 6.54 (2H, d, J = 2.0 Hz, H-2'/6'), 6.28 (1H, br s, H-4'), 3.78 (3H, s, OCH$_3$)<br>$^{13}$C-NMR (75 MHz, CD$_3$OD) δ 162.6 (C-5'), 159.8 (C-3'), 146.5 (C-4), 146.3 (C-3), 144.8 (C-1'), 134.7 (C-1), 119.5 (C-6), 116.6 (C-5), 115.1 (C-2), 107.3 (C-6'), 104.9 (C-2'), 100.5 (C-4'), 55.7 (OCH$_3$) |

As shown in FIGS. 2-5 and Table 1, the analyses results identified that the compound of Chemical Formula 1 is a novel compound including a biphenyl group.

Experimental Example 1

Determination of the Inhibitory Effect of Novel Compound on AGE Formation

To determine the inhibitory effect of the compound of Chemical Formula 1 according to the present invention on formation of AGE, which are an indicator of diabetic complications and indicator of treatment efficiency assessment, the following experiment was carried out.

Bovine serum albumin (BSA) was used as a protein and the degree of binding to fructose and glucose was used as an indicator. Aminoguanidine, which is known to have very excellent inhibitory effect on AGE, was used as a positive control.

Bovine serum albumin (hereinafter, referred to as BSA; Sigma, U.S.A.) was used as a protein source. BSA was added to 50 mM phosphate buffer (pH 7.4) to be a concentration of 10 mg/mL. A mixed solution of 0.2 M fructose and 0.2 M glucose was used as a sugar source. The mixed solution of fructose and glucose was added to the prepared BSA solution. 2.5, 5 and 10 μg/mL of the compound of Chemical Formula 1 obtained from Example 1 were prepared (All compounds were dissolved in DMSO and 15% tween 80 was added thereto. Total amount of DMSO was 0.2%). The compound was added to the mixed solution of BSA and sugars and the mixture was cultured at 37° C. for 7 days.

At this time, 0.02% sodium azide and anticomycotics were added as an antibacterial agent and antifungal agents. A control was the cultured mixture of BSA and sugars. Blanks for the control and experimental group were those that were prepared but non-cultured. Aminoguanidine was used for a positive control, the indicator for comparing the effectiveness. All cultures were prepared in quadruplicate to avoid error as much as possible.

After 7 days, the amount of AGE produced from each culture was analyzed and the result was shown. AGE has fluorescence, brown color, and a physicochemical property capable of cross-linking and has ligands which cell membrane receptors can recognize. The amount of AGE having those characteristics was measured by a microplate reader (Excitation: 350 nm, Emission: 450 nm) to analyze the inhibition degree of formation (Vinson, J. A. et al., *J. Nutr. Biochem.*, 7: 659-663, 1996), and the inhibition rate of formation was calculated using the following Equation 1.

Aminoguanidine was used for the positive control. Aminoguanidine was dissolved in distilled water and 37, 55.6. and 74 μg/mL of aminoguanidine were cultured for 7 days as described above. After 7 days, the amount of AGE produced from culture was measured by a microplate reader (Excitation: 350 nm, Emission: 450 nm). The result was shown in the following Table 2.

[Equation 1]

The inhibition rate of formation (%) =

$$100 - \frac{\text{(Fluorescence Intensity of Experimental Group} - \text{Fluorescence Intensity of Blank for Experimental Group)}}{\text{(Fluorescence Intensity of Control} - \text{Fluorescence Intensity of Blank for Control)}} \times 100$$

TABLE 2

| | 7 days | | |
|---|---|---|---|
| | Conc. (μg/mL) | Inhibitory effect (%) | IC$_{50}$ (μM) |
| Compound of Chemical Formula 1 | 2.5 | 4.25 ± 5.38 | 41.00 ± 3.78 μM |
| | 5 | 17.16 ± 5.86 | |
| | 10 | 54.17 ± 6.02 | |
| Aminoguanidine (control) | 37 | 44.53 ± 2.33 | 1056.47 ± 57.25 μM |
| | 55.5 | 49.97 ± 0.59 | |
| | 74 | 56.37 ± 0.67 | |

As shown in Table 2, the experimental group treated with the compound of Chemical Formula 1 according to the present invention showed 41.00±3.78 μM of IC$_{50}$ value and had the inhibitory effect on AGE formation, which was 26 times greater than that of the control, aminoguanidine.

Accordingly, the novel biphenyl compound inhibited the binding of proteins and sugars, and had excellent inhibitory effect on AGE formation, and thus, it can be used effectively for prevention, treatment, or amelioration of diabetic complications or cancers caused by AGE.

Experimental Example 2

Determination of Effects in Diabetic Retinopathy-Induced Diabetes Animal Model To determine the therapeutic effect of the compound of the present invention on retina, to which diabetic retinopathy, one example of diabetic complications, was induced, the following experiment was carried out.

Step 1: Preparation of Diabetic Retinopathy-Induced Experimental Animals

Sprague Dawley (SD) white rats (6 weeks) were obtained from Daehan Biolink Co. and acclimated for 7 days to the animal room. SD rats were divided into normal group, diabetic group, experimental group, and control group. The animal room was maintained under the following conditions: temperature 23° C.; humidity 40-60%; and 12 h light-dark cycle. Feeds for experimental animals and drinking water were provided without limitation. All experiments were carried out in accordance with Standard Operation Procedures (SOP) by Institutional Animal Care and Use Committee (IACUC).

SD rats were anesthetized by an intraperitoneal injection of 5 mg/mL of Zoletil and 5 mg/mL of Rompun. 20 mg/mL of BSA-AGE alone for normal group and diabetic group and both 20 mg/mL of BSA-AGE and a drug for experimental group and control group were injected via Hamilton syringes and needles to eyes. At this time, the needle was introduced into the sclera, 3 mm away from the corneal limbus, and after confirming that the end of the needle was located in the vitreous cavity, administration was carried out. After 24 hours, eyes were removed. The compound of Chemical Formula 1 obtained from Example 1 was used for the drug.

A mixture of the same amount of Zoletil and Rompun was intraperitoneally injected to anesthetize animals. Hearts were obtained by opening abdominal cavity and thoracic cavity. 1 mL of fluorescent isothiocyanate dextran (FITC-dextran, Sigma, St. Louis, Mo., USA) which was prepared by dissolving 50 mL of FITC-dextran in 1 mL of sterile physiological saline was injected into the left ventricle. After 10 minutes, eyes were removed and separated from eyecups. Left eyes were incised in four directions and placed onto a slide glass. After mounting, left eyes were observed by a fluorescent microscope. For right eyes, only retina was separated from the eye and rapidly frozen in liquid nitrogen and stored at −70° C.

Step 2: BSA-AGE Preparation

To prepare BSA-AGE, 30 mM glucose (Sigma, St. Louis, Mo., USA) and 20 mg/mL of BSA (Roche, Germany) were added to sodium phosphate buffer (100 mM, pH 7.4) and cultured at 37° C. for 50 days.

After 50 days, BSA-AGE was injected into PD-10 column and the remaining glucose was removed by dialysis and only pure BSA-AGE was obtained. Purified BSA-AGE was aliquoted and stored at −70° C. to use.

Step 3: Western Blot Analysis

Retina stored at −70° C. was homogenized with homogenization buffer (pH 7.6). Protein quantification was carried out by Lowry's principle and SDS-PAGE electrophoresis was carried out for each 30 mL. Migrated proteins in a gel were immobilized onto a nitrocellulose membrane and transferred to the membrane at 100 V, 250 mA for 1.5 hours.

Antibodies to be quantified were immunoabsorbed to the adsorbed proteins and color was developed using an enhanced-chemiluminescence (ECL) solution. Protein expression was determined by measuring the density with Scion image analysis program. The result was shown below.

Result (1) Changes in Retinal Vessels

Figure 6:
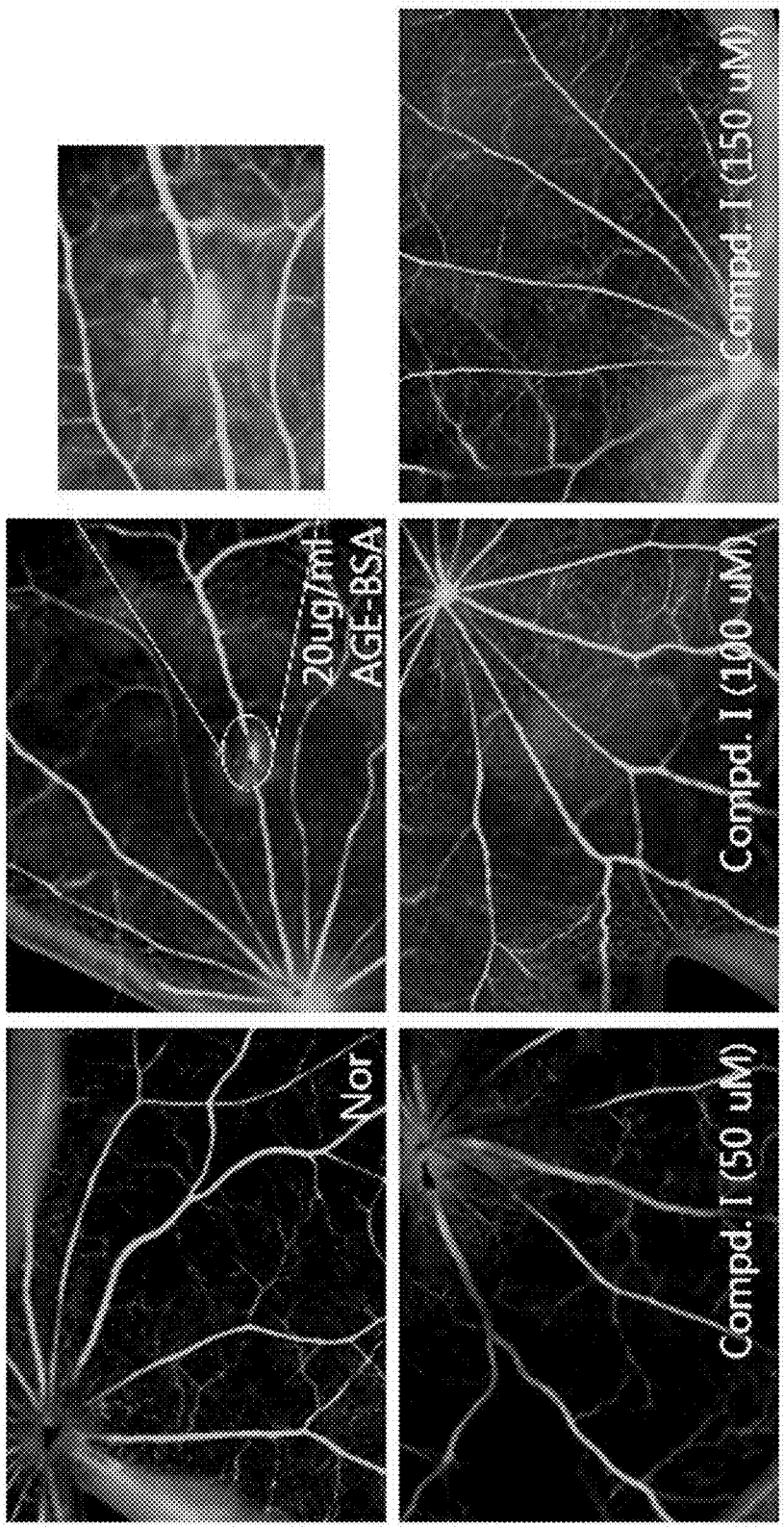
FIG. 6 is a drawing showing changes in blood vessels of retina by the compound of Chemical Formula 1 according to one example of the present invention.

When the fluorescent substance (FITC-dextran) was injected to experimental animals in each group (normal group, diabetic group, and experimental group) and retinal vessels were observed, as shown in FIG. 6, no abnormality was observed in normal group. The breakdown of the blood-retinal barrier was observed in the diabetic group where diabetic retinopathy was induced with 20 μg/mL of BSA-AGE. On the other hand, the experimental group which was treated with 100 μM or 150 μM of the compound of Chemical Formula 1 according to the present invention was similar to the normal group where no symptoms were observed (see FIG. 6).

(2) Changes in Occludin

Figure 7:
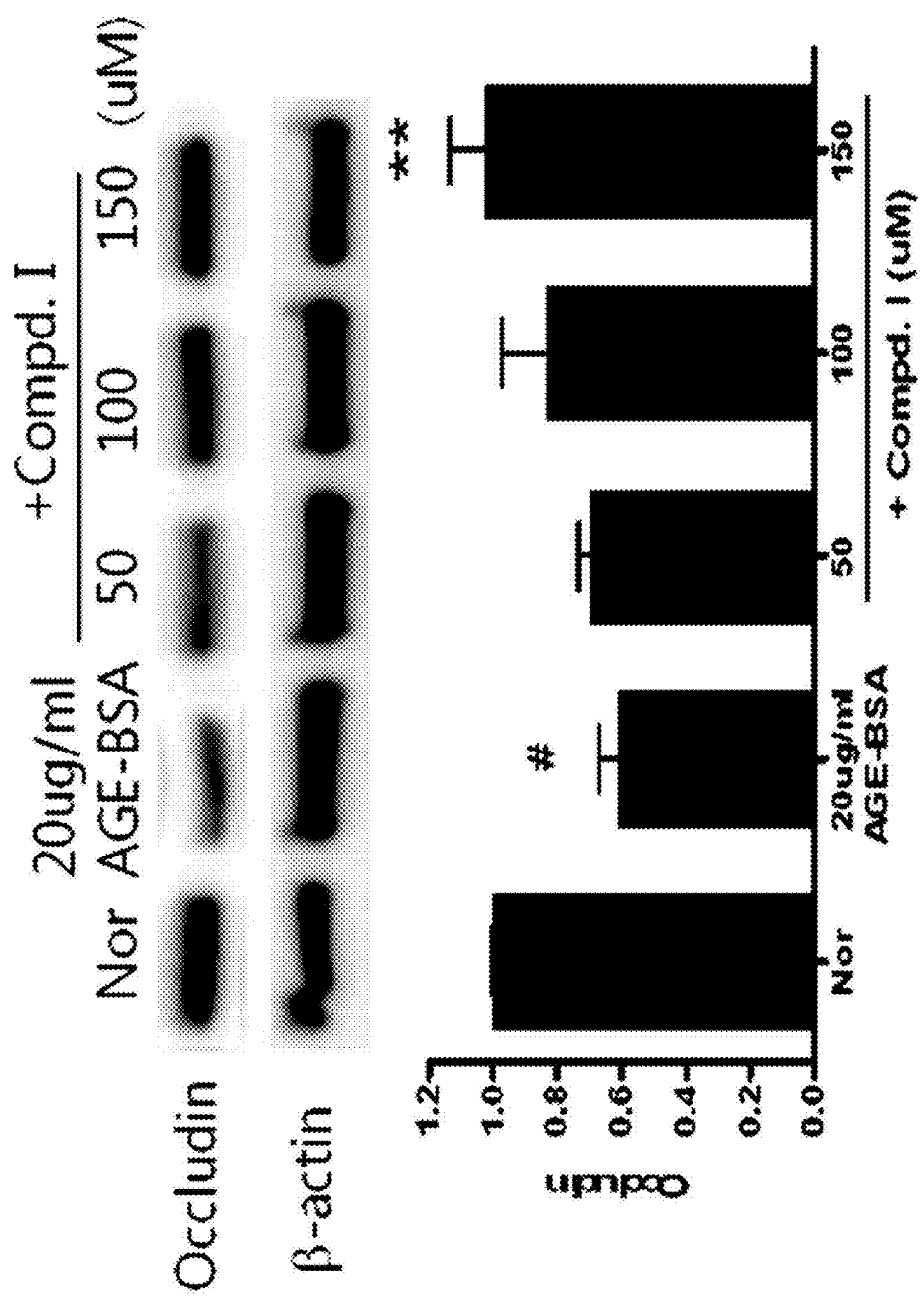
FIG. 7 is a drawing showing changes in occludin by the compound of Chemical Formula 1 according to one example of the present invention.

Changes in occludin, the protein constituting the tight junction, which is a water-tight protective barrier for eyes, were measured. Consequently, as shown in FIG. 7, occludin was reduced significantly in the diabetic group compared to the normal group ($p<0.01$ vs. Nor). However, the experimental group treated with the compound of Chemical Formula 1 of the present invention showed a dose-dependent increase in occludin, and particularly, 100 μM and 150 μM concentrations showed a significant increase ($p<0.05$ vs. AGE-BSA) (see FIG. 7).

(3) Changes in the Angiogenic Growth Factor

Figure 8:
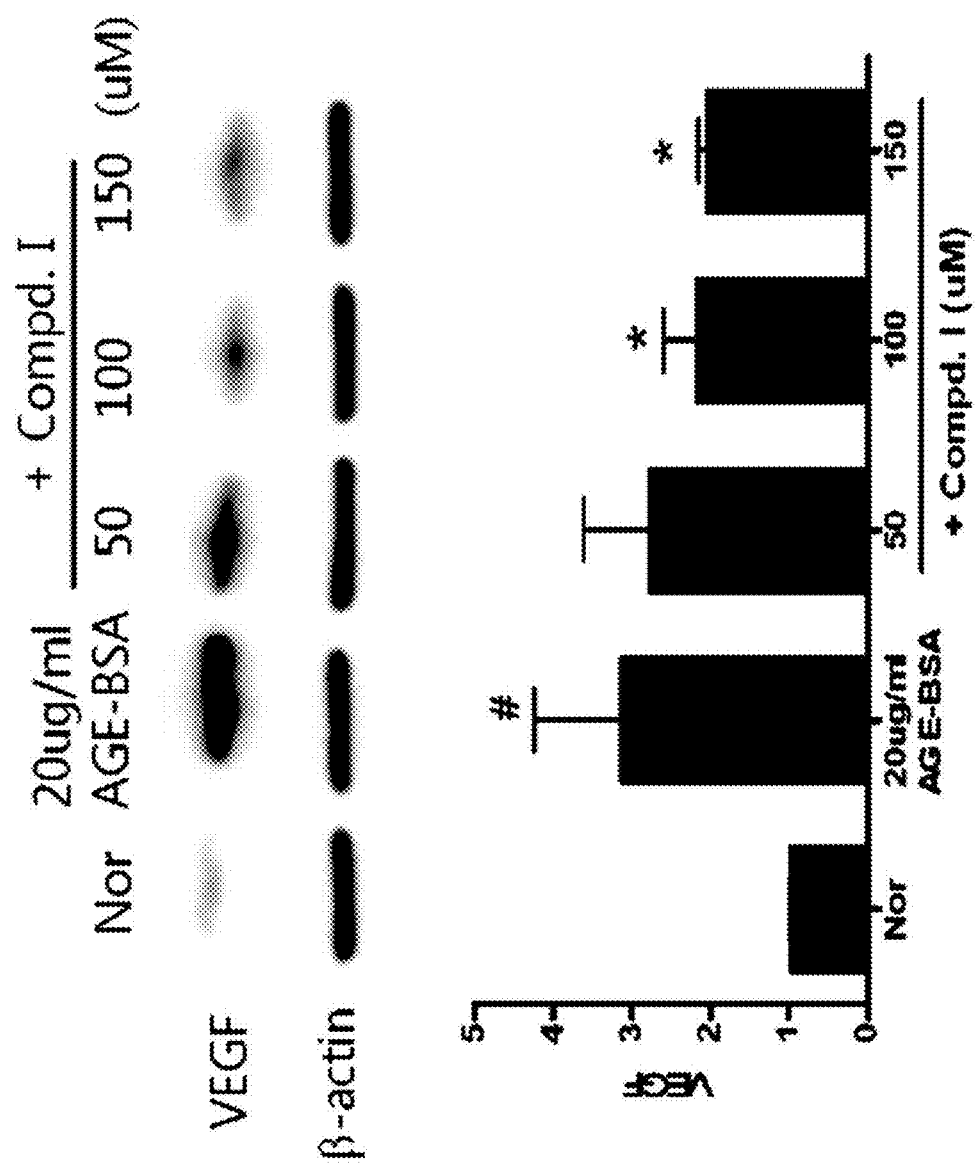
FIG. 8 is a drawing showing changes in the angiogenic factor by the compound of Chemical Formula 1 according to one example of the present invention.

Changes in the angiogenic growth factor were measured. Consequently, as shown in FIG. 8, the diabetic group showed a remarkable increase in the angiogenic growth factor compared to the normal group ($p<0.01$ vs. Nor). However, the group treated with the compound of Chemical Formula 1 of the present invention showed a dose-dependent decrease, and particularly, 100 μM and 150 μM concentrations showed a significant decrease ($p<0.05$ vs. AGE-BSA) (see FIG. 8).

Accordingly, the novel biphenyl compound of the present invention prevented the breakdown of blood-retinal barrier, caused an increase in occludin, the protein constituting the tight junction, and caused a significant decrease in the angiogenic growth factor in experimental animals in which diabetic complications such as diabetic retinopathy were induced, and thus, it can be used effectively for the prevention, treatment, or amelioration of diabetic complications or cancers.

Experimental Example 3

Determination of Preventive Effect on Retinal Angiogenesis Using Oxygen Induced Retinopathy (OIR) Mouse Model To determine the inhibitory effect of the compound of Chemical Formula 1 of the present invention on retinal angiogenesis, the following experiment was carried out.

Step 1: Experimental Animal Preparation and Retinopathy Induction

Experimental animals were mice born after crossbreeding 7-8-week-old C58BL/6. On 7th day after birth, mice (P7) were placed into an oxygen chamber and 75% of the oxygen concentration was maintained in the chamber for five days (P7-P11). 12-hour cyclic illumination was maintained in the animal room. Temperature was maintained at 24° C. Animals were allowed to access freely to feeds and drinking water. At an ambient atmosphere, the drug was intraperitoneally injected each day for five days (P12-P16).

Step 2: Observation of Changes in Retinal Vessels

On $17^{th}$ day after birth, 30 mg/kg of Zoletil (Zoletil 50, Virbac) and 10 mg/kg of Rompun (Bayer Korea) were mixed at a ratio of 3:2 and 10-fold diluted in physiological saline and 50 µL was intraperitoneally injected to anesthetize animals. After laparotomy, 100 µL of 50 mg/mL of FITC-dextran (Sigma, St. Louis, Mo., USA) dissolved in PBS was injected to a heart. When the heart stopped, eyes were removed. Retina was separated from one eye and stored at −70° C. The other eye was fixed using 4% paraformaldehyde for 10 min. After separation of retina, thin fixed retina slide was prepared and observed using a fluorescence microscope (BX51, Olympus, Japan).

Step 3: Staining with Isolectin-B4, a Marker Specific for Retinal Blood Vessels

Retina was fixed in 4% paraformaldehyde for 3 hours, and washed with PBS, and then agitated in PBS containing triton X-100 and 1% bovine serum albumin for 3 hours. Retina was washed again and 1 mg/mL of isolectin-B4 (L2140, Sigma) was diluted in PBS to 1:50 and retina was agitated with isolectin-B4 at 4° C. for overnight. After washing the retina with PBS containing 0.05% Tween 20 for 2 hours, streptavidin-TRITC was diluted to 1:500 and allowed to react with retina at 37° C. for 4 hours. Then, retina was washed with PBS for 30 min and observed using a fluorescence microscope (BX51, Olympus, Japan).

Step 4: Western Blot Analysis

Retina stored at −70° C. was homogenized with homogenization buffer (pH 7.6). Protein quantification was carried out by Lowry's principle and SDS-PAGE electrophoresis was carried out for each 30 µg. Migrated proteins in a gel were immobilized onto a nitrocellulose membrane and transferred to the membrane at 100 V, 250 mA for 1.5 hours.

Antibodies to be quantified were immunoabsorbed to the adsorbed proteins and color was developed using an enhanced-chemiluminescence (ECL) solution. Protein expression was determined by measuring the density with Scion image analysis program. The result was shown below.

Results (1) Changes in Retinal Vessels

Figure 9:
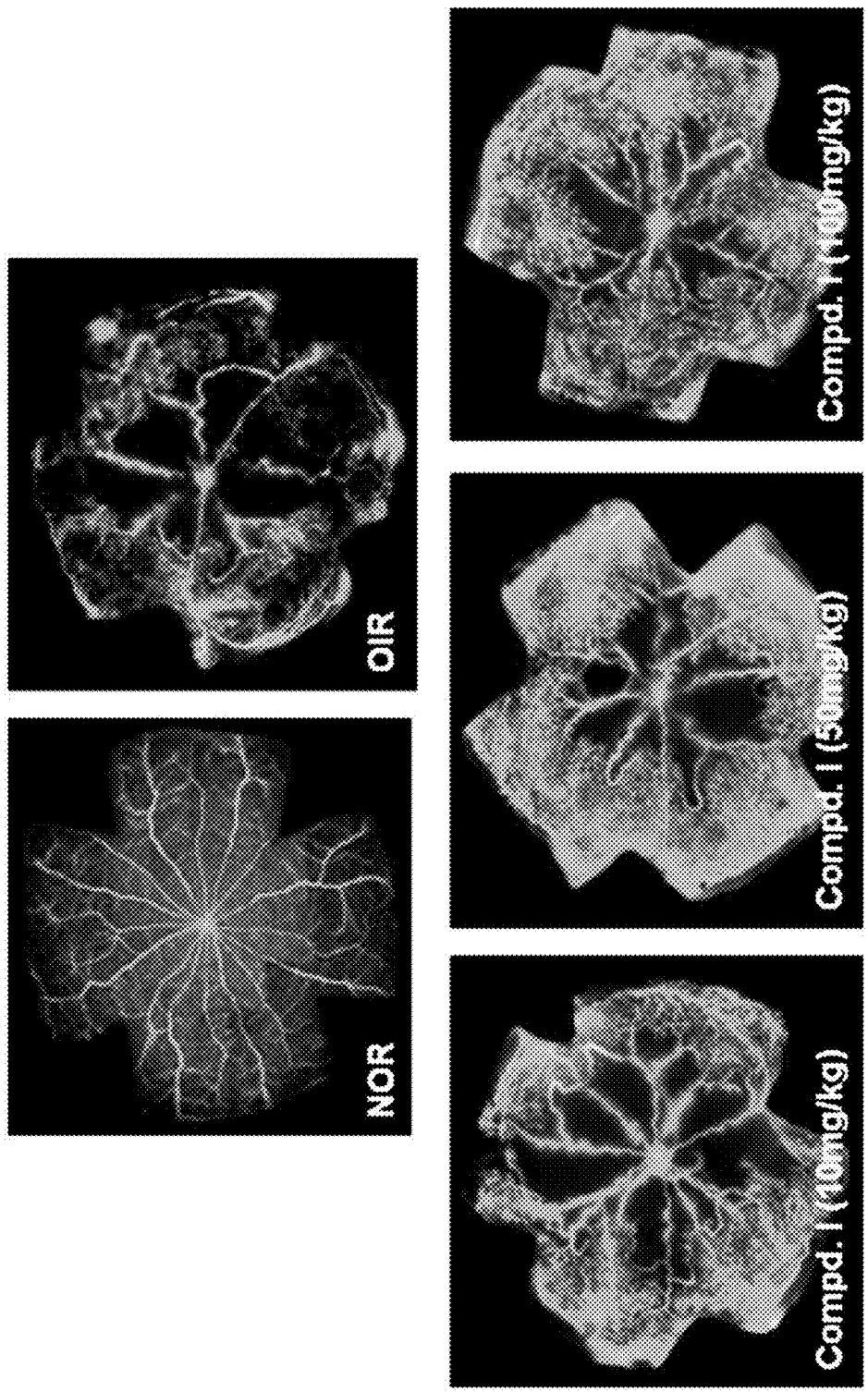
FIG. 9 is a drawing showing changes in blood vessels of retina in an OIR model by the compound of Chemical Formula 1 according to one example of the present invention.

When the fluorescent substance (FITC-dextran) was injected to experimental animals in each group (normal group, OIR group, and experimental group) and retinal vessels were observed, as shown in FIG. 9, no abnormality was observed in normal group (NOR). In the OIR group, the phenomenon in which retinal capillaries disappear around the optic disk (avascular area) was observed, and vascular tortuosity, which is caused by blood vessel weakening induced by retinopathy in the remaining arterial and venous blood from where capillaries disappear, was often observed.

However, vascular tortuosity in the group treated with the compound of Chemical Formula 1 of the present invention was ameliorated in a dose-dependent manner, and particularly, in the group treated with 100 mg/kg of the compound, avascular area was significantly reduced, and the increase in length by vascular tortuosity was also reduced (see FIG. 9).

Figure 10:
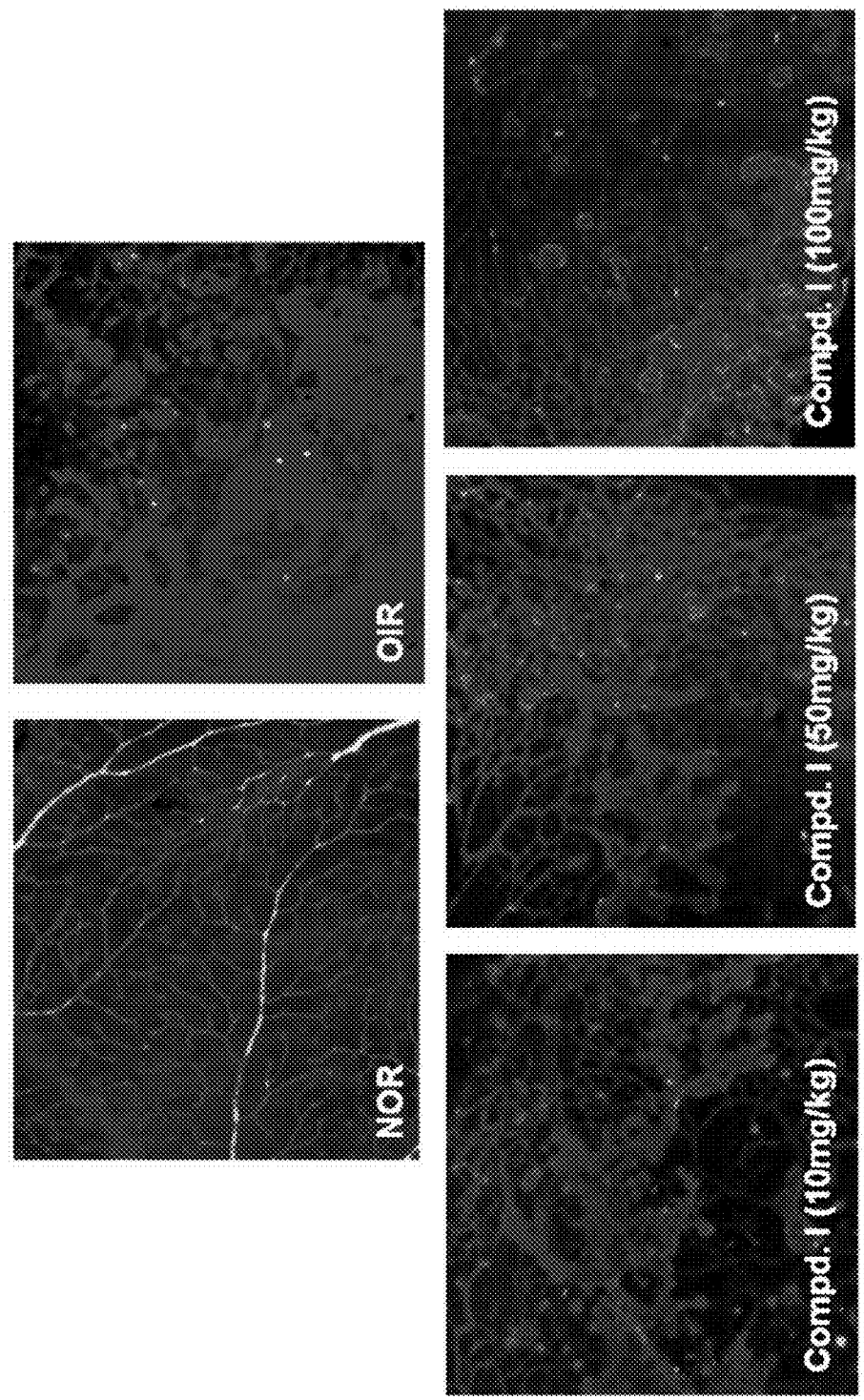
FIG. 10 is a drawing showing changes in angiogenesis in blood vessels of retina in an OIR model by the compound of Chemical Formula 1 according to one example of the present invention.

In addition, when retinopathy is induced by high concentration of oxygen, neovascular tufts are generated around inner retina adjacent to vitreous. As shown in FIG. 10, staining with specific marker isolectin-B4 was carried out to observe these neovascular tufts. As a result, newly generated neovascular tufts, which covered normal vasculature, were observed. Meanwhile, the phenomena were ameliorated in a dose-dependent manner in the group treated with the compound of Chemical Formula 1 of the present invention, and particularly, angiogenesis was significantly inhibited in the group treated with 100 mg/kg of the compound (see FIG. 10).

(2) Changes in the Angiogenic Growth Factor

Figure 11:
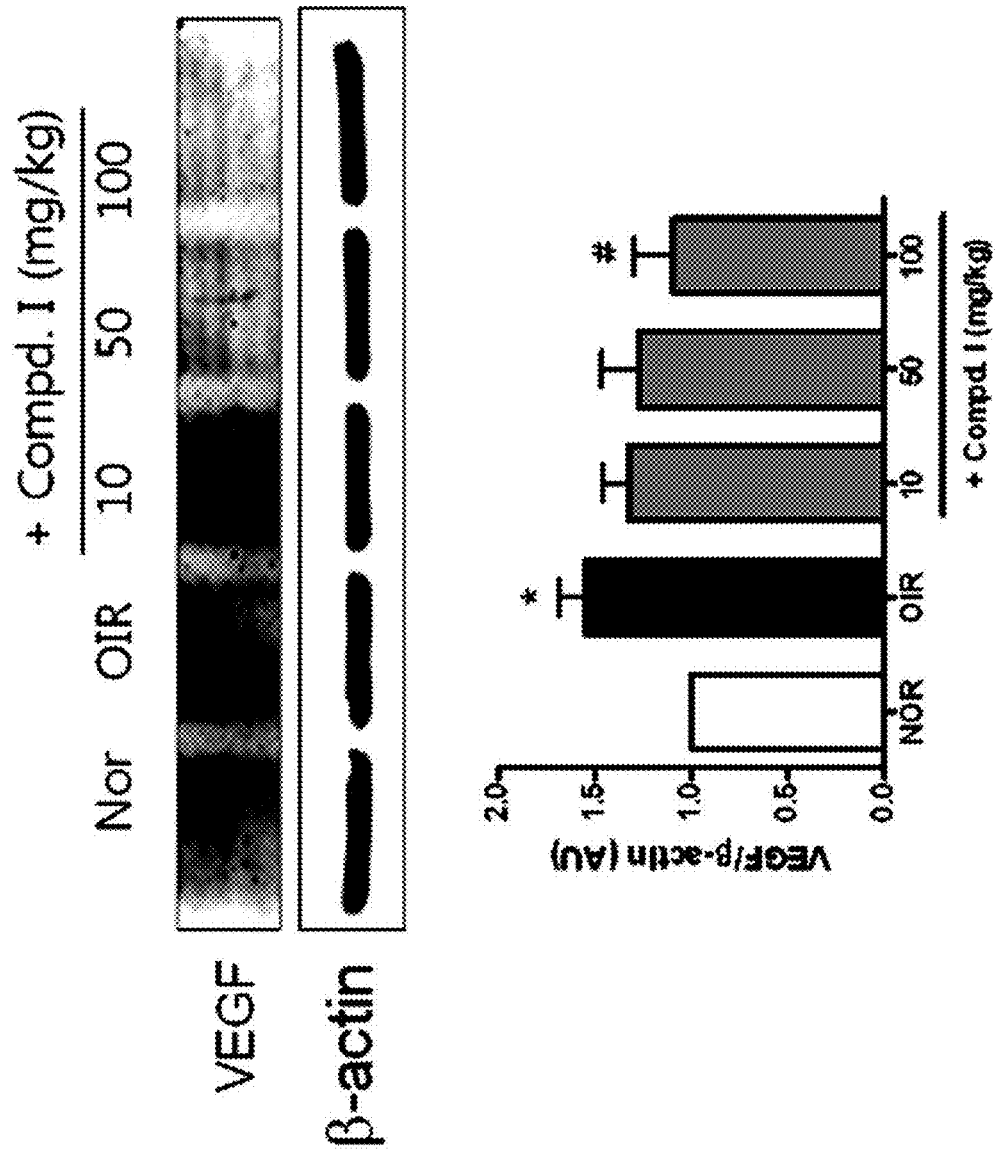
FIG. 11 is a drawing showing changes in the angiogenic factor in an OIR model by the compound of Chemical Formula 1 according to one example of the present invention.

Changes in the angiogenic growth factor were measured. Consequently, as shown in FIG. 11, the OIR group showed a remarkable increase in the angiogenic growth factor compared to the normal group ($p<0.01$ vs. Nor). However, the group treated with the compound of Chemical Formula 1 of the present invention showed a dose-dependent decrease, and particularly, the group at 100 mg/kg concentration showed a significant decrease ($p<0.05$ vs. OIR) (see FIG. 11).

Accordingly, the novel biphenyl compound of the present invention effectively inhibited angiogenesis by reducing the angiogenic growth factor (VEGF) in the oxygen induced diabetic retinopathy animal model, and thus, it can be used effectively for the prevention, treatment, or amelioration of diabetic complications or diabetic cancers.

Preparation Example 1

Preparation of Pharmaceutical Formulations

<1-1> Powder Preparation 500 mg of novel biphenyl compound
100 mg of lactose
10 mg of talc The above ingredients are mixed, and filled into an airtight bag to prepare a powder.

<1-2> Tablet Preparation 500 mg of novel biphenyl compound
100 mg of corn starch
100 mg of lactose
2 mg of magnesium stearate The above ingredients are mixed, and tabletted by a conventional tablet preparation method to prepare a tablet.

<1-3> Capsule Preparation 500 mg of novel biphenyl compound
100 mg of corn starch
100 mg of lactose
2 mg of magnesium stearate The above ingredients are mixed by a conventional capsule preparation method, and filled in a gelatin capsule to prepare a capsule.

<1-4> Injection Preparation 500 mg of novel biphenyl compound
Suitable amount of sterile distilled water for injection
Suitable amount of a pH regulator One ampoule (2 mL) is prepared with the above contents of the ingredients by a conventional injection preparation method.

<1-5> Liquid Preparation 100 mg of novel biphenyl compound
10 g of isomerized sugar
5 g of mannitol
Suitable amount of purified water According to a conventional liquid preparation method, each ingredient is added to purified water and dissolved therein, and lemon flavor is added thereto in a suitable amount. And then, the above ingredients are mixed and purified water added thereto so that the total amount become 100 mL, and filled in a brown bottle and sterilized to prepare a liquid.

Formulation Example 2

Health Food Preparation 1000 mg of novel biphenyl compound
Suitable amount of vitamin mixture
70 µg of vitamin A acetate
1.0 mg of vitamin E
0.13 mg of vitamin $B_1$
0.15 mg of vitamin $B_2$ 0.5 mg of vitamin $B_6$
0.2 μg of vitamin $B_{12}$
10 mg of vitamin C
10 μg of biotin
1.7 mg of nicotinic acid amide
50 mg of folic acid
0.5 mg of calcium pantothenate
Suitable amount of mineral mixture
1.75 mg of ferrous sulfate
0.82 mg of zinc oxide
25.3 mg of magnesium carbonate
15 mg of calcium phosphate, monobasic
55 mg of calcium phosphate, dibasic
90 mg of potassium citrate
100 mg of calcium carbonate
24.8 mg of magnesium chloride The above ratio of vitamins and minerals illustrates a preferable example of mixing ingredients relatively suitable for a health food; however, it can be modified arbitrarily. According to a conventional health food preparation method, the above ingredients are mixed, and granules are prepared and used for preparation of a health food composition by a conventional method.

Formulation Example 3

Health Beverage Preparation 1000 mg of novel biphenyl compound
1000 mg of citrate
100 g of oligosaccharides
2 g of Japanese apricot concentrate
1 g of taurine
Purified water to adjust the volume to 900 mL The above ingredients were mixed according to a conventional health beverage preparation method, and heated with agitation at 85° C. for about 1 h, and then, the prepared solution was filtered to obtain in a sterilized 2 L vessel, seal sterilized and refrigeration stored to use for the health beverage composition of the present invention.

The above ratio illustrates a preferable example of mixing ingredients relatively suitable for a favorite beverage; however, it can be modified arbitrarily according to regional and ethnic preferences such as of the class of consumers or consumer country, the uses, etc.

Formulation Example 4

Other Health Foods Preparation

<4-1> Drink Preparation
522 mg of honey
5 mg of thioctic acid amide
10 mg of nicotinic acid amide
3 mg of riboflavin sodium chloride
2 mg of pyridoxine hydrochloride
30 mg of inositol
50 mg of orotate
0.48-1.28 mg of novel biphenyl compound
200 mL of water Drink was prepared with the above amounts of ingredients by a conventional method.
<4-2> Chewing Gum Preparation
20% of gum base
76.36-76.76% of sugar
0.24-0.64% of novel biphenyl compound
1% of fruits flavor
2% of water A chewing gum was prepared with the above amounts of ingredients by a conventional method.
<4-3> Candy Preparation
50-60% of sugar
39.26-49.66% of starchy syrup
0.24-0.64% of novel biphenyl compound
0.1% of orange flavor A candy was prepared with the above amounts of ingredients by a conventional method.
<4-4> Flour Food Preparation A food for health improvement was prepared by adding 0.5 to 5% by weight of the novel biphenyl compound to 100 5 by weight of wheat flour, and then making bread, cakes, cookies, crackers and noodles using the mixture.
<4-5> Dairy Products Preparation Various dairy products such as butter and ice cream were prepared by adding 5 to 10% by weight of the novel biphenyl compound to 100% by weight of milk and using the mixture.
<4-6> Grain Powder Preparation Brown rice, barley, glutinous rice and *coix* (job's tear) were gelatinized by a known method, followed by drying. The dried mixture was distributed and pulverized, resulting in 60-mesh size grain powders. Black bean, black sesame and *perilla* were steamed and dried by a known method. The dried mixture was distributed and pulverized, resulting in 60-mesh size grain powders. The prepared grain, seeds, and the novel biphenyl compound of the present invention were all mixed at the following ratio.

30% of brown rice
15% of *coix*
20% of barley
7% of *perilla*
7% of black bean
7% of black sesame
3% of novel biphenyl compound
0.5% of *Ganoderma lucidum*
0.5% of *Rehmannia glutinosa*

What is claimed is:
1. A biphenyl compound represented by the following Chemical Formula 1 or a pharmaceutically acceptable salt thereof:

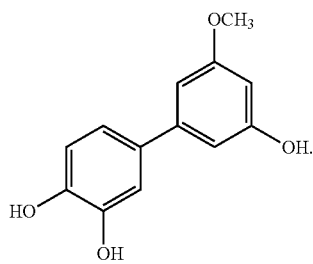

[Chemical Formula 1]

2. A method for preparing a biphenyl compound of claim 1, the method comprising the steps of:
(1) extracting *Osteomeles schwerinae* Schneid with water, an alcohol, or a mixture thereof to obtain *Osteomeles schwerinae* Schneid extract;
(2) suspending the *Osteomeles schwerinae* Schneid extract obtained from step (1) in water and then obtaining n-hexane, ethyl acetate, and n-butanol fractions of *Osteomeles schwerinae* Schneid by stepwise using n-hexane, ethyl acetate and n-butanol as an extraction solvent;

(3) carrying out a silica gel column chromatography on the ethyl acetate fraction of *Osteomeles schwerinae* Schneid obtained from step (2) to separate and purify an active fraction; and (4) carrying out Sephadex LH-20 column chromatography on the active fraction obtained from step (3) to separate and purify the compound represented by Chemical Formula 1 of claim 1.

3. A pharmaceutical composition for treating diabetic complications, the composition containing the biphenyl compound represented by Chemical Formula 1 of claim 1 or a pharmaceutically acceptable salt thereof as an active ingredient.

4. The composition as set forth in claim 3, wherein diabetic complications are diabetic retinopathy, diabetic cataract, diabetic nephropathy, diabetic neuropathy, diabetic heart diseases, diabetic osteoporosis, or diabetic atherosclerosis.

5. A health food composition for ameliorating diabetic complications, containing the biphenyl compound represented by Chemical Formula 1 of claim 1 or a pharmaceutically acceptable salt thereof as an active ingredient.

6. The composition as set forth in claim 5, wherein diabetic complications are diabetic retinopathy, diabetic cataract, diabetic nephropathy, diabetic neuropathy, diabetic heart diseases, diabetic osteoporosis, or diabetic atherosclerosis.

7. A method for treating diabetic complications, comprising administering the biphenyl compound represented by Chemical Formula 1 of claim 1 or pharmaceutically acceptable salt thereof to a patient in need thereof.

8. The biphenyl compound represented by Chemical Formula 1 of claim 1 or pharmaceutically acceptable salt thereof, which are used for treating diabetic complications.

\* \* \* \* \*